(12) United States Patent
Shuros et al.

(10) Patent No.: US 9,186,080 B2
(45) Date of Patent: Nov. 17, 2015

(54) SYSTEM FOR IDENTIFYING ROTOR PROPAGATION VECTORS

(71) Applicant: Boston Scientific Scimed Inc., Maple Grove, MN (US)

(72) Inventors: Allan C. Shuros, St. Paul, MN (US); Pramodsingh H. Thakur, White Bear Lake, MN (US); Shibaji Shome, Arden Hills, MN (US); Barun Maskara, Blaine, MN (US); Shantha Arcot-Krishnamurthy, Vadnais Heights, MN (US); Sunipa Saha, Shoreview, MN (US); Jacob Laughner, St. Paul, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 14/272,292

(22) Filed: May 7, 2014

(65) Prior Publication Data
US 2014/0336518 A1  Nov. 13, 2014

Related U.S. Application Data

(60) Provisional application No. 61/820,599, filed on May 7, 2013.

(51) Int. Cl.
| | |
|---|---|
| *A61B 5/04* | (2006.01) |
| *A61B 5/00* | (2006.01) |
| *A61B 5/042* | (2006.01) |
| *A61B 5/046* | (2006.01) |

(52) U.S. Cl.
CPC ........... *A61B 5/04012* (2013.01); *A61B 5/0422* (2013.01); *A61B 5/6858* (2013.01); *A61B 5/7246* (2013.01); *A61B 5/046* (2013.01)

(58) Field of Classification Search
None
See application file for complete search history.

(56) References Cited

U.S. PATENT DOCUMENTS

| | | | |
|---|---|---|---|
| 5,647,870 | A | 7/1997 | Kordis et al. |
| 6,070,094 | A | 5/2000 | Swanson et al. |
| 6,233,491 | B1 | 5/2001 | Kordis et al. |
| 6,735,465 | B2 | 5/2004 | Panescu |
| 7,123,954 | B2 | 10/2006 | Narayan et al. |

(Continued)

FOREIGN PATENT DOCUMENTS

WO  2012092016 A1  7/2012

OTHER PUBLICATIONS

Houben, Richard P.M. et al., "Processing Intracardiac Electrograms in Atrial Fibrillation", Diagosis of Electropathological Substrate of AF, IEEE Engineering in Medicine and Biology Magazine, Nov./Dec. 2006, pp. 40-51.

(Continued)

*Primary Examiner* — Brian T Gedeon
*Assistant Examiner* — Ankit Tejani
(74) *Attorney, Agent, or Firm* — Faegre Baker Daniels LLP (57) ABSTRACT

A method and system for mapping an anatomical structure includes sensing activation signals of intrinsic physiological activity with a plurality of mapping electrodes disposed in or near the anatomical structure. The activation signals are used to determine a dominant frequency for each electrode from which a wavefront vector for each electrode is determined based on a difference between the dominant frequency at a first electrode location and the dominant frequency at neighboring electrodes. An anatomical map is generated based on the determined wavefront vectors.

20 Claims, 4 Drawing Sheets (56) References Cited

U.S. PATENT DOCUMENTS

2004/0059237 A1    3/2004   Narayan et al.
2007/0021679 A1    1/2007   Narayan et al.
2011/0275949 A1   11/2011   Harlev et al.
2012/0232417 A1*   9/2012   Zhang ........................... 600/518

OTHER PUBLICATIONS

International Search Report and Written Opinion issued in PCT/US2014/034189, mailed Sep. 8, 20014, 12 pages.

Sra, Jasbir et al., "Mapping Techniques for Atrial Fibrillation Abaltion", Current Problems in Cardiology, vol. 32, No. 12, Nov. 2007, pp. 669-767.

* cited by examiner

SYSTEM FOR IDENTIFYING ROTOR PROPAGATION VECTORS

CROSS-REFERENCE TO RELATED APPLICATION

This application claims priority to Provisional Application No. 61/820,599, filed May 7, 2013, which is herein incorporated by reference in its entirety.

TECHNICAL FIELD

The present invention relates to medical devices and methods for accessing an anatomical space of the body. More specifically, the invention relates to devices and methods for generating vector field maps of electrical activity of anatomical structures.

BACKGROUND

Diagnosing and treating heart rhythm disorders often involve the introduction of a catheter having a plurality of sensors/probes into a cardiac chamber through the surrounding vasculature. The sensors detect electric activity of the heart at sensor locations in the heart. The electric activity is generally processed into electrogram signals that represent signal propagation through cardiac tissue at the sensor locations.

Systems can be configured to display the electrical signals detected in the cardiac chamber as an activation map based on voltages detected. Robust and reliable estimation of onset times for sensed activation signals is the key to visualizing underlying activation patterns and identify targets for applying therapy, e.g. ablation therapy. Mapping electrograms during a manifestation of a heart rhythm disorder, such as fibrillation, can be used to identify a dominant frequency and thus estimate the location of a source of the aberrant activity based on visible patterns. However, sensed activation signals can be very noisy due to several factors including, but not limited to, movement of mapping electrodes relative to the tissue of the anatomical structure of interest, far-field activation signals, and the like. The noise can introduce artifacts into the visualization and mapping of the electrograms and thus interfering with the detection of apparent patterns. There exists a need to determine and enhance the detection of local patterns in electrograms.

Traditional methods use characteristic features of the activation signals such as steepest descent for a unipolar signal or most negative peak of a derivative unipolar signal. Any characteristic feature is susceptible to ambiguity stemming from noise or other artifacts, such as a far-field activation signal or multiple large negative peaks adjacent to one another, which superimpose over the signal of interest. There exists a need to improve the reliability of detection of onset times of activation signals in anatomical mapping.

SUMMARY

In Example 1, a method for mapping an anatomical structure includes sensing activation signals of intrinsic physiological activity with a plurality of mapping electrodes disposed in or near the anatomical structure, each of the plurality of mapping electrodes having an electrode location, determining a dominant frequency at each electrode location, and determining a wavefront vector at each electrode location based on a difference between the dominant frequency at a first electrode location and the dominant frequency at neighboring electrode locations.

In Example 2, the method according to Example 1, further includes determining a propagation vector at each electrode location based on a bipolar signal of a sensed activation signal between adjacent electrodes, each propagation vector represents a direction of propagation of the activation signal at the corresponding electrode location, and determining a correlation vector at each electrode location based on a correlation of the wavefront vector and propagation vector at the corresponding electrode location.

In Example 3, the method according to either of Examples 1 and 2, wherein the correlation of the wavefront and propagation vector is based on at least one of circular average, an inner-product of corresponding angles, and a trigonometric relationship of corresponding angles.

In Example 4, the method according to any of Examples 1-3, further includes identifying propagation patterns in the correlated vectors for all electrode locations for each sensed activation signal.

In Example 5, the method according to any of Examples 1-4, wherein determining the dominant frequency further includes transforming the sensed activation signals at each electrode location to a frequency domain signal with a plurality of frequency components, and identifying the frequency component with the highest amplitude.

In Example 6, the method according to any of Examples 1-5, wherein determining a wavefront vector further includes determining a vector based on a change of the dominant frequency between adjacent electrodes, and calculating a sum of all vectors at each electrode location.

In Example 7, the method according to any of Examples 1-6, further includes displaying an anatomical map based on determined wavefront vectors at each electrode location.

In Example 8, a method for mapping an anatomical structure includes sensing activation signals of intrinsic physiological activity with a plurality of mapping electrodes disposed in or near the anatomical structure, each of the plurality of mapping electrodes having an electrode location, determining a wavefront vector at each electrode location based on a difference between a dominant frequency at a first electrode location and a dominant frequency at adjacent electrode locations, determining a propagation vector at each electrode location based on a bipolar signal of the sensed activation signals between adjacent electrode locations, each propagation vector represents a direction of propagation of the activation signal at the corresponding electrode location, and determining a correlation vector at each electrode location based on a correlation between a wavefront vector and a propagation vector at the corresponding electrode location.

In Example 9, the method of Example 8 further includes generating a correlation map based on the correlation vector at each electrode location, and identifying propagation patterns in the correlated map indicative of a pathology of the anatomical structure.

In Example 10, the method according to either of Examples 8 and 9, further includes generating a display including at least one of the correlation map and the identified propagation patterns.

In Example 11, the method according to any of Examples 8-10, wherein the correlation between the wavefront and propagation vector is based on at least one of circular average, an inner-product of corresponding angles, and a trigonometric relationship of corresponding angles.

In Example 12, the method according to any of Examples 8-11, wherein determining the dominant frequency further includes transforming the sensed activation signals at each electrode location to a frequency domain signal with a plurality of frequency components, and identifying the frequency component with the highest amplitude.

In Example 13, the method according to any of Examples 8-12, wherein determining a wavefront vector further includes determining a vector based on a change of the dominant frequency between adjacent electrodes, and calculating the sum of all vectors at each electrode location.

In Example 14, a catheter system includes a plurality of mapping electrodes disposed in or near an anatomical structure configured to detect activation signals of physiological activity, each of the plurality of mapping electrodes having an electrode location, and a processing system associated with the plurality of mapping electrodes, the processing system configured to record the detected activation signals and associate one of the plurality of mapping electrodes with each recorded activation signal, the processing system further configured to determine a dominant frequency at each electrode location, and determine a wavefront vector at each electrode location based on a difference between the dominant frequency at a first electrode location and the dominant frequency at neighboring electrode locations.

In Example 15, the catheter system of Example 14, wherein the processing system is further configured to determine a propagation vector at each electrode location based on a bipolar signal of a sensed activation signal between adjacent electrodes, each propagation vector represents a direction of propagation of the activation signal at the corresponding electrode location, and determine a correlation vector at each electrode location based on a correlation of the wavefront vector and propagation vector at the corresponding electrode location.

In Example 16, the catheter system of either Examples 14 and 15, wherein the processing system is further configured to identify propagation patterns in the correlated vectors for all electrode locations for each sensed activation signal.

In Example 17, the catheter system of any of Examples 14-16, wherein to determine the dominant frequency, the processing system is further configured to transform the sensed activation signals at each electrode location to a frequency domain signal with a plurality of frequency components, and identify the frequency component with the highest amplitude.

In Example 18, the catheter system of any of Examples 14-17, wherein to determine a wavefront vector, the processing system is further configured to determine a vector based on a change of the dominant frequency between adjacent electrodes, and to calculate a sum of all vectors at each electrode location.

In Examples 19, the catheter system of any of Examples 14-18, further includes displaying an anatomical map generated based on determined wavefront vectors at each electrode location.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
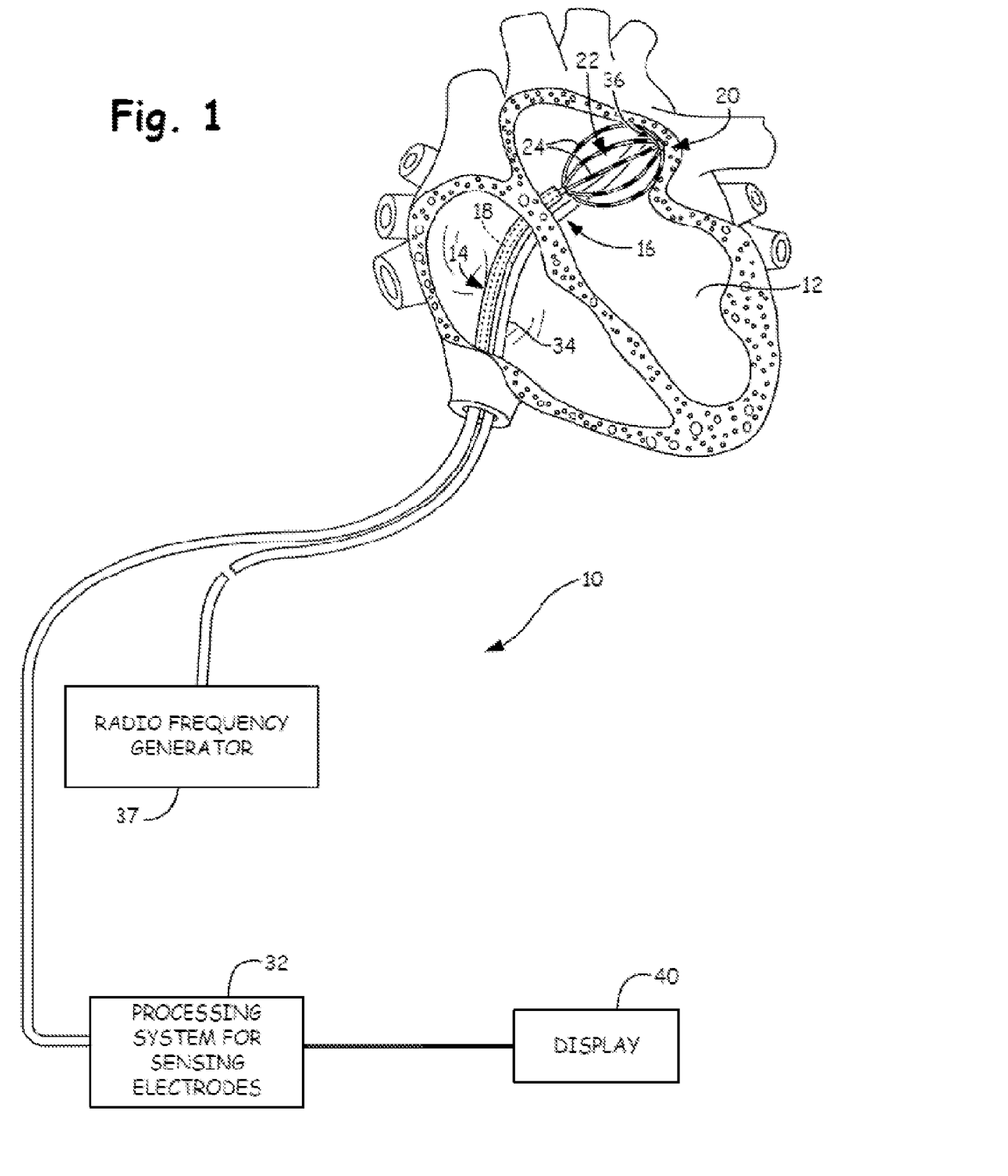
FIG. 1 is a schematic view of an embodiment of a system for accessing a targeted tissue region in the body for diagnostic and therapeutic purposes.

FIG. 1 is a schematic view of a system 10 for accessing a targeted tissue region in the body for diagnostic or therapeutic purposes. FIG. 1 generally shows the system 10 deployed in the left atrium of the heart. Alternatively, system 10 can be deployed in other regions of the heart, such as the left ventricle, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 can be assembled in an integrated structure for simultaneous introduction and deployment in the heart region 12.

The mapping probe 14 has a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations are known. The multiple electrode structure 20 carries a plurality of mapping electrodes 24 each having an electrode location and channel. Each electrode 24 is configured to sense intrinsic physiological activity in the anatomical region on which the ablation procedure is to be performed. In some embodiments, the electrodes 24 are configured to detect activation signals of the intrinsic physiological activity within the anatomical structure, e.g., the activation times of cardiac activity.

The electrodes 24 are electrically coupled to a processing system 32. A signal wire (not shown) is electrically coupled to each electrode 24 on the basket structure 20. The wires extend through the body 18 of the probe 14 and electrically couple each electrode 24 to an input of the processing system 32, as will be described later in greater detail. The electrodes 24 sense intrinsic electrical activity in the anatomical region, e.g., myocardial tissue. The sensed activity, e.g. activation signals, is processed by the processing system 32 to assist the physician by generating an anatomical map, e.g., a vector field map, to identify the site or sites within the heart appropriate for ablation. The processing system 32 identifies a near-field signal component, i.e. activation signals associated with local activation and originating from the tissue adjacent to the mapping electrode 24, from an obstructive far-field signal component, i.e. activation signals originating from non-adjacent tissue, within the sensed activation signals. For example, in an atrial study, the near-field signal component includes activation signals originating from atrial myocardial tissue whereas the far-field signal component includes activation signals originating from the ventricular myocardial tissue. The near-field activation signal component can be further analyzed to find the presence of a pathology and to determine a location suitable for ablation for treatment of the pathology, e.g., ablation therapy.

The processing system 32 includes dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired activation signals. In some embodiments, the processing system 32 includes a general purpose microprocessor and/or a specialized microprocessor (e.g., a digital signal processor, or DSP, which may be optimized for processing activation signals) that executes instructions to receive, analyze and display information associated with the received activation signals. In such implementations, the processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that the processing system 32 can take any suitable form.

In some embodiments, the processing system 32 may be configured to measure the intrinsic electrical activity in the myocardial tissue adjacent to the electrodes 24. For example, in some embodiments, the processing system 32 is configured to detect intrinsic electrical activity associated with a dominant rotor or divergent activation pattern in the anatomical feature being mapped. Studies have shown that dominant rotors and/or divergent activation patterns have a role in the initiation and maintenance of atrial fibrillation, and ablation of the rotor path, rotor core, and/or divergent foci may be effective in terminating the atrial fibrillation. In either situation, the processing system 32 processes the sensed activation signals to generate a display of relevant characteristic, such as an APD map, a vector field map, a contour map, a reliability map, an electrogram, and the like. The relevant characteristics may be used by the physician to identify a site suitable for ablation therapy.

The ablation probe 16 includes a flexible catheter body 34 that carries one or more ablation electrodes 36. The one or more ablation electrodes 36 are electrically connected to a radio frequency generator (RF) 37 that is configured to deliver ablation energy to the one or more ablation electrodes 36. The ablation probe 16 is movable with respect to the anatomical feature to be treated, as well as the structure 20. The ablation probe 16 is positionable between or adjacent to electrodes 24 of the structure 20 as the one or more ablation electrodes 36 are positioned with respect to the tissue to be treated.

The processing system 32 outputs to a device 40 the display of relevant characteristics for viewing by a physician. In the illustrated embodiment, device 40 is a CRT, LED, or other type of display, or a printer). The device 40 presents the relevant characteristics in a format most useful to the physician. In addition, the processing system 32 may generate position-identifying output for display on the device 40 that aids the physician in guiding the ablation electrode(s) 36 into contact with tissue at the site identified for ablation.

Figure 2:
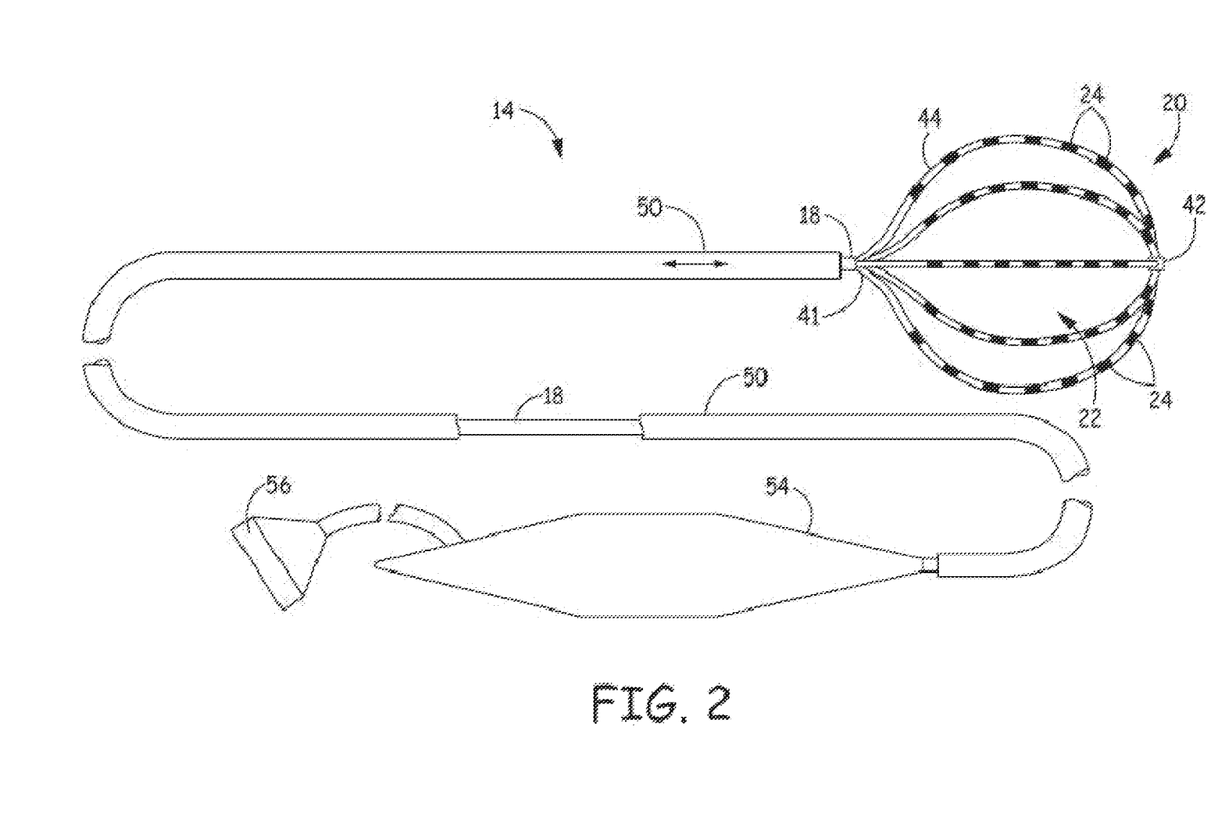
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity, e.g., activation signals, in the myocardial tissue, the sensed activity is then processed by the processing system 32 to assist the physician in identifying the site or sites having a heart rhythm disorder or other myocardial pathology via a generated and displayed relevant characteristics. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is even smaller or larger (e.g., 40 mm in diameter or greater).

A slidable sheath 50 is movable along the major axis of the catheter body 18. Moving the sheath 50 forward (i.e., toward the distal end) causes the sheath 50 to move over the three dimensional structure 20, thereby collapsing the structure 20 into a compact, low profile condition suitable for introduction into and/or removal from an interior space of an anatomical structure, such as, for example, the heart. In contrast, moving the sheath 50 rearward (i.e., toward the proximal end) exposes the three dimensional structure 20, allowing the structure 20 to elastically expand and assume the pretensed position illustrated in FIG. 2. Further details of embodiments of the three dimensional structure 20 are disclosed in U.S. Pat. No. 5,647,870, entitled "Multiple Electrode Support Structures," which is hereby expressly incorporated herein by reference in its entirety.

A signal wire (not shown) is electrically coupled to each mapping electrode 24. The wires extend through the body 18 of the mapping catheter 20 into a handle 54, in which they are coupled to an external connector 56, which may be a multiple pin connector. The connector 56 electrically couples the mapping electrodes 24 to the processing system 32. Further details on mapping systems and methods for processing signals generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are hereby expressly incorporated herein by reference.

It is noted that other multi-electrode structures could be deployed on the distal end of the mapping catheter 14. It is further noted that the multiple mapping electrodes 24 may be disposed on more than one structure rather than, for example, the single mapping catheter 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping catheter 14, the mapping electrodes may be carried on non-mapping dedicated probes or multifunction probes. For example, an ablation catheter, such as the ablation catheter 16, can be configured to include one or more mapping electrodes 24 disposed on the distal end of the catheter body and coupled to the signal processing system 32 and guidance system (not shown). As another example, the ablation electrode at the distal end of the ablation catheter may be coupled to the signal processing system 32 to also operate as a mapping electrode.

Figure 3:
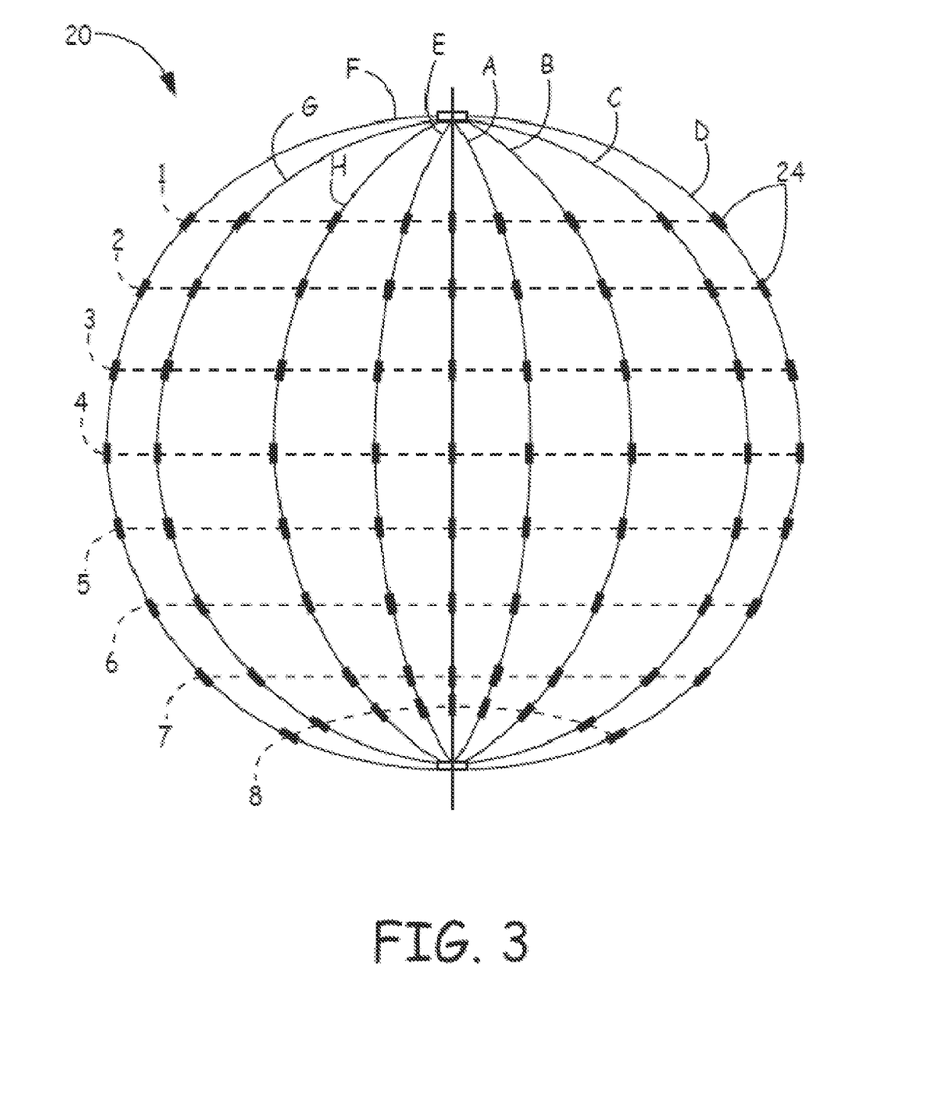
FIG. 3 is a schematic side view of an embodiment of the basket functional element including a plurality of mapping electrodes.

To illustrate the operation of the system 10, FIG. 3 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers, on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated (e.g., left atrium or left ventricle of the heart), the processing system 32 is configured to record the activation signals from each electrode 24 channel related to intrinsic physiological activity of the anatomical structure, i.e. the electrodes 24 measure electrical activation signals intrinsic to the physiology of the anatomical structure.

The processing system 32 is configured to identify propagation patterns to identify dominant rotor, rotor pathway, and/or divergent activity within the sensed activation signals. In embodiments, after sensing the activation signals, the processing system 32 determines a dominant frequency at each electrode location for each sensed activation signal. The dominant frequency at each electrode location is determined based on a frequency component of the activation signal with the highest amplitude. To determine the dominant frequency, the processing system 32 transforms each sensed activation signal, a time domain signal, into a frequency domain signal via a Fourier transform to generate a plurality of frequency components which define the activation signal. The processing system 32 determines which frequency has the greatest amplitude at each electrode location as the dominant frequency at that corresponding electrode location for the given activation signal. In some embodiments, the processing system 32 can generate a dominant frequency map for display on the display device 40. Dominant frequency analysis from dominant frequency maps are effective tools used to understand pathophysiology of an anatomical structure.

The processing system 32 determines a wavefront vector at each electrode location based on the determined dominant frequency at the corresponding electrode location. The processing system 32 calculates a vector difference between the dominant frequency at a first electrode location and each of the neighboring electrodes. The user can select the number of neighboring electrode locations the processing system 32 uses to calculate the difference. For example, the user may select eight neighboring electrodes which includes four orthogonal & four diagonal electrode locations, four neighboring electrodes which includes four orthogonal electrode locations, or four neighboring electrodes which includes four diagonal electrode locations. The number of selected neighboring electrode locations can impact a processing time and number of compute cycles the processing system 32 employs to determine each wavefront vector. After the difference vector is calculated between the neighboring electrodes, the processing system 32 calculates a sum of the neighboring difference vectors to determine the resultant wavefront vector. This is repeated for all electrode locations to generate a vector field of wavefront vectors. Typically, the wavefront vectors of the vector field will point to the highest dominant frequency. However, this may not always be the case. In some embodiments, the processing system 32 is configured to display the wavefront vector field on the display device 40 for inspection by a physician or a user of the anatomical mapping system 10. The wavefront vector field can identify regions of high frequency activity in the anatomical structure. In the example of cardiac fibrillation, a region undergoing high frequency activity can be indicative of aberrant activity related to a cardiac pathology, e.g. fibrillation, and related to a dominant rotor, rotor pathway, or divergent activity.

In embodiments, the processing system 32 determines a propagation vector at each electrode location based on a bipolar signal between a first mapping electrode 24 at a first electrode location and neighboring mapping electrodes 24. The user can select the number of neighboring electrode locations the processing system 32 uses to calculate the bipolar signal. For example, the user may select eight neighboring electrodes which includes four orthogonal & four diagonal electrode locations, four neighboring electrodes which includes four orthogonal electrode locations, or four neighboring electrodes which includes four diagonal electrode locations. The polarity of each bipolar pair of mapping electrodes 24 is used to determine the direction of the propagation of the activation signal. For example, if the polarity of the propagation vector is positive then the direction of propagation is towards the positive electrode. Conversely, if the polarity is negative then the direction of propagation is away from the positive electrode. An isoelectric polarity indicates that the direction of propagation is perpendicular to the bipolar pair of electrodes 24. The system 10 may be configured in a unipolar sensing arrangement in which the bipolar signal is determined according to a difference between adjacent unipolar signals, i.e. sensed activation signals. In some embodiments, the system 10 includes a common return electrode in electrical communication with the processing system 32 to sense bipolar activation signals at each electrode location sequentially. In this arrangement, the processing system 32 can determine the wavefront propagation vectors using the mapping electrode 24 arrangement of FIG. 3, then determine a propagation vector for each electrode location sequentially with a bipolar return electrode arranged separately from the multi-electrode structure 20, e.g. an external ECG electrode (not shown). The processing system 32 can sense both unipolar and bipolar activation signals to improve signal to noise ratio at each electrode location and for each sensed activation signal.

The processing system 32 repeats the process to determine a propagation vector at each electrode location. In some embodiments, the processing system 32 is configured to generate a propagation vector field which can be displayed on the display device 40 for inspection by a user and/or physician.

According to embodiments, another methodology for finding local propagation vectors includes calculating the conduction velocity vectors for a subset of electrodes (e.g., a 3×3 neighborhood of electrodes). The median conduction velocity vector of the local neighborhood may be used to represent the conduction velocity of the center electrode. This process may be repeated for each electrode in an overlapping fashion. In embodiments, this methodology acts as a spatial filter to remove small errors in a global conduction velocity map. Once conduction velocity vectors are determined for all electrodes in the multi-electrode array, the divergence and vorticity of the velocity field may be provided for diagnostic purposes. The divergence of the velocity vector field may show potential ectopic foci for ablation targeting. Additionally, the vorticity calculation may show potential rotational cores indicative of macro reentrant and micro reentrant rotations.

In various embodiments, the processing system 32 determines a correlation vector at each electrode location based on a correlation between a wavefront vector and a propagation vector at an electrode location for each activation signal. After an activation signal is sensed or detected, the processing system 32 determines the wavefront and propagation vector at each electrode location sequentially or simultaneously. The processing system 32 correlates the determined wavefront and propagation vector at each corresponding electrode location to further enhance detection of pathophysiological patterns. Certain characteristics of pathophysiological activity may manifest themselves more readily in the correlation vectors rather than in the wavefront and/or propagation vectors alone to generate a correlation vector field. The processing system 32 repeats the correlation at each electrode location. In some embodiments, the processing system 32 is configured to display the correlation vector field on the display device 40. In one example, the direction of the correlation vector is based on a circular average between the wavefront vector and propagation vector, The magnitude of the correlation vector can be determined to ensure that if the wavefront vector and the propagation vector do not coincide, the overall correlation vector is reduce to zero. In one embodiment, the magnitude or distance of the correlation vector is based on an inner-product between unit vectors which represent the wavefront and propagation vectors. The magnitude is one if the vectors or collinear and zero if the vectors are orthogonal or if the inner product is negative. Alternatively, a cosine of the angle between the wavefront vector and propagation vector can be employed to determine the magnitude of the correlation vector.

The processing system 32 can use the correlation vectors and/or the correlation vector field to identify propagation patterns in the correlation vectors. The propagation patterns in the correlation vectors can yield insight on pathologies associated with the anatomical structure of interest. In some embodiments, the processing systems 32 can use template matching algorithms to match the correlation vector field to a bank of vector field templates. The templates may include information regarding, for example, a rotor, rotor pathway, and/or divergent electrical activity along with a point of origin or focal point which can be used to diagnose a pathology and recommend a treatment location in or near the anatomical structure. The processing system is configured to use other digital signal processing algorithms to match the correlation vector field map to a known template or to identify known patterns among the correlation vectors. In addition, the processing system 32 can use the signal processing algorithms on the wavefront vectors and corresponding wavefront vector field and the propagation vectors and corresponding propagation vector field to identify patterns associated with a related or unrelated pathology.

It should be appreciated that the processing system 32 can generate the wavefront vectors, propagation vectors, and corresponding correlation vectors based on a single sensed activation signal or with multiple activation signals that are averaged over time. Furthermore, activation signal amplitudes across the multiple mapping electrodes 24 of the structure 20 may not be consistent due to manufacturing faults, tissue contact faults and/or difficulties, movement, noise, and the like. The processing system 32 is configured to normalize sensed activation signals across the mapping electrodes to values between −1 and +1 to account for the influence of inconsistent amplitudes. After signals are normalized, the processing system 32 can determine any one or all of the wavefront, propagation, and correlations vectors along with corresponding vector fields.

Figure 4:
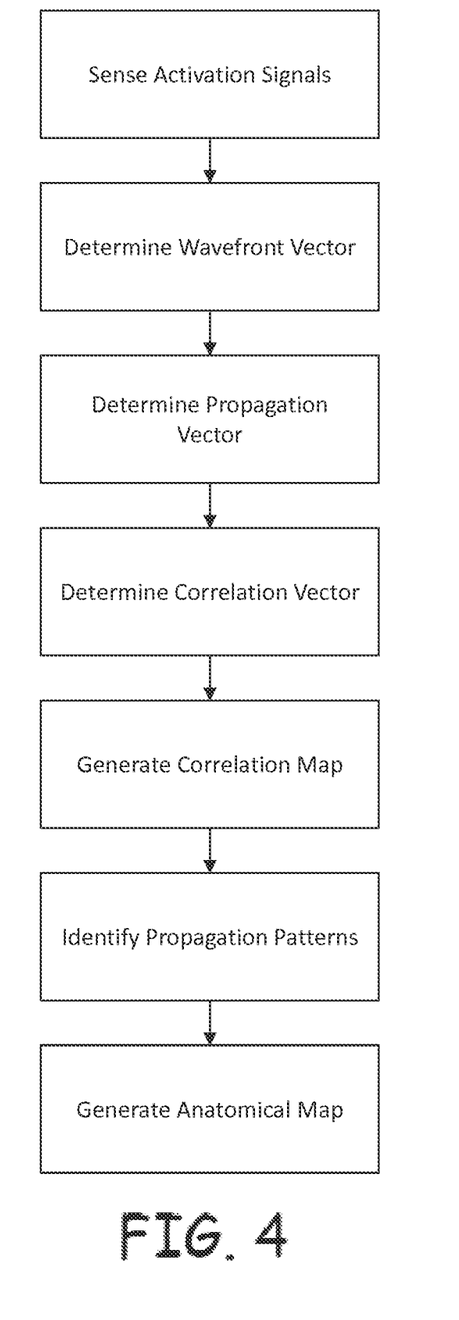
FIG. 4 is a flow chart illustrating a method of mapping an anatomical structure (e.g., the heart) according to one embodiment.

The system 10 is configured to perform a method of mapping an anatomical structure as illustrated in FIG. 4. After the mapping electrodes 24 are disposed in or adjacent to an anatomical structure, e.g. cardiac tissue, the system 10 senses electrical activation signals associated with intrinsic physiological activity of the anatomical structure. The system 10 determines a wavefront vector at each electrode location based on a difference between a dominant frequency at a first electrode location and a dominant frequency at least one adjacent electrode location. The dominant frequency at each electrode is determined according to a frequency domain transformation and identification of the frequency component(s) with the highest amplitude. A propagation vector is determined at each electrode location based on a bipolar signal of the sensed activation signals between the corresponding electrode location and adjacent electrode locations. Each propagation vector represents a direction of propagation of the activation signal at the corresponding electrode location. The system 10 determines a correlation vector at each electrode location based on a correlation between a wavefront vector and a propagation vector at the corresponding electrode location and a correlation map is generated base on the correlation vectors determined for each electrode location. Propagation patterns are identified in the correlated map which may be indicative of a pathology of the anatomical structure. The system 10 can compare the correlation map to one or more templates of a bank of vector field templates using template matching algorithms to identify a corresponding pattern. Any one of a wavefront vector field, propagation vector field, correlation vector field, identified propagation patterns, and any combination thereof can be displayed on the display device 40.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for mapping an anatomical structure, the method comprising:
sensing activation signals of intrinsic physiological activity with a plurality of mapping electrodes disposed in or near the anatomical structure, each of the plurality of mapping electrodes having an electrode location;
determining a dominant frequency for each sensed activation signal at each electrode location;
determining a plurality of difference vectors at each electrode location, wherein a difference vector of the plurality of difference vectors for a respective electrode location represents a difference between the dominant frequency of a sensed activation signal at the respective electrode location and the dominant frequency of a sensed activation signal at a neighboring electrode location; and
determining a wavefront vector at each electrode location based on the plurality of difference vectors.

2. The method according to claim 1, further including:
determining a propagation vector at each electrode location based on a bipolar signal of a sensed activation signal between adjacent electrodes, each propagation vector represents a direction of propagation of the activation signal at the corresponding electrode location; and
determining a correlation vector at each electrode location based on a correlation of the wavefront vector and propagation vector at the corresponding electrode location.

3. The method according to claim 2, wherein the correlation of the wavefront and propagation vector is based on at least one of circular average, an inner-product of corresponding angles, and a trigonometric relationship of corresponding angles.

4. The method according to claim 2, further including:
identifying propagation patterns in the correlated vectors for all electrode locations for each sensed activation signal.

5. The method according to claim 1, wherein determining the dominant frequency further includes:
transforming the sensed activation signals at each electrode location to a frequency domain signal with a plurality of frequency components; and
identifying the frequency component with the highest amplitude.

6. The method according to claim 1, wherein determining a wavefront vector further includes:
determining a vector based on a change of the dominant frequency between adjacent electrodes; and
calculating a sum of all vectors at each electrode location.

7. The method according to claim 1, further including:
displaying an anatomical map based on determined wavefront vectors at each electrode location.

8. A method for mapping an anatomical structure, the method comprising:
sensing activation signals of intrinsic physiological activity with a plurality of mapping electrodes disposed in or near the anatomical structure, each of the plurality of mapping electrodes having an electrode location;
determining a plurality of difference vectors at each electrode location, wherein a difference vector of the plurality of difference vectors for a respective electrode location represents a difference between a dominant frequency of a sensed activation signal at the respective electrode location and a dominant frequency of a sensed activation signal at a neighboring electrode location; and
determining a wavefront vector at each electrode location based on the plurality of difference vectors;
determining a propagation vector at each electrode location based on a bipolar signal of the sensed activation signals between adjacent electrode locations, each propagation vector represents a direction of propagation of the activation signal at the corresponding electrode location; and
determining a correlation vector at each electrode location based on a correlation between the wavefront vector and the propagation vector at the corresponding electrode location.

9. The method of claim 8, further including:
generating a correlation map based on the correlation vector at each electrode location; and
identifying propagation patterns in the correlated map indicative of a pathology of the anatomical structure.

10. The method according to claim 9, further including:
generating a display including at least one of the correlation map and the identified propagation patterns.

11. The method according to claim 8, wherein the correlation between the wavefront and propagation vector is based on at least one of circular average, an inner-product of corresponding angles, and a trigonometric relationship of corresponding angles.

12. The method of claim 8, wherein determining the dominant frequency further includes:
transforming the sensed activation signals at each electrode location to a frequency domain signal with a plurality of frequency components; and
identifying the frequency component with the highest amplitude.

13. The method according to claim 8, wherein determining a wavefront vector further includes:
determining a vector based on a change of the dominant frequency between adjacent electrodes; and
calculating the sum of all vectors at each electrode location.

14. A catheter system comprising:
a plurality of mapping electrodes disposed in or near an anatomical structure configured to detect activation signals of physiological activity, each of the plurality of mapping electrodes having an electrode location;
a processing system associated with the plurality of mapping electrodes, the processing system configured to record the detected activation signals and associate one of the plurality of mapping electrodes with each recorded activation signal, the processing system further configured to determine a dominant frequency of each recorded activation signal at each electrode location, determine a plurality of difference vectors at each electrode location, wherein a difference vector of the plurality of difference vectors for a respective electrode location represents a difference between the dominant frequency of a recorded activation signal at the respective electrode location and the dominant frequency of a recorded activation signal at a neighboring electrode location, and determine a wavefront vector at each electrode location based on the plurality of difference vectors.

15. The catheter system of claim 14, wherein the processing system is further configured to determine a propagation vector at each electrode location based on a bipolar signal of a sensed activation signal between adjacent electrodes, wherein each propagation vector represents a direction of propagation of the activation signal at the corresponding electrode location, and determine a correlation vector at each electrode location based on a correlation of the wavefront vector and propagation vector at the corresponding electrode location.

16. The catheter system of claim 14, wherein the processing system is further configured to determine a propagation vector at each electrode location based on a median conduction velocity vector associated with a plurality of neighboring electrodes.

17. The catheter system of claim 15, wherein the processing system is further configured to identify propagation patterns in the correlated vectors for all electrode locations for each sensed activation signal.

18. The catheter system of claim 14, wherein to determine the dominant frequency, the processing system is further configured to transform the sensed activation signals at each electrode location to a frequency domain signal with a plurality of frequency components, and identify the frequency component with the highest amplitude.

19. The catheter system of claim 14, wherein to determine a wavefront vector, the processing system is further configured to determine a vector based on a change of the dominant frequency between adjacent electrodes, and to calculate a sum of all vectors at each electrode location.

20. The catheter system of claim 14, further including:
displaying an anatomical map generated based on determined wavefront vectors at each electrode location.

* * * * *